United States Patent [19]

Faierstein et al.

[11] 3,986,264

[45] Oct. 19, 1976

[54] DENTURE PROSTHETICS TOOL

[76] Inventors: Samuel Faierstein, 1003 St. Joseph Boulevard, East, Montreal, Quebec; Bernard Farkas, 3202 Van Horne Ave., 3202 Van Horne Avenue, Canada

[22] Filed: Oct. 7, 1974

[21] Appl. No.: 512,496

[52] U.S. Cl. ............................................. 32/40 R
[51] Int. Cl.² ........................................... A61C 3/00
[58] Field of Search ............. 128/305, 304; 30/305, 30/115; 32/40 R, 46, 70

[56] References Cited
UNITED STATES PATENTS

| | | | |
|---|---|---|---|
| 877,813 | 1/1908 | Waller | 30/304 |
| 1,503,610 | 8/1924 | Smith | 32/50 |
| 1,913,800 | 6/1933 | Farquhar | 30/305 |
| 2,013,902 | 9/1935 | Tarrant | 30/304 |

FOREIGN PATENTS OR APPLICATIONS 130,497  2/1927  Switzerland ........................... 32/70

*Primary Examiner*—Robert Peshock

[57] ABSTRACT

A tool adapted for use in the dental art for denture prosthetics and distinctively to perform relatively faster heat softening of the gum-shape piece of wax currently used to take an imprint of one's mouth. This tool includes an elongated handle, a service blade and a multi-bladed spatula with the service blade either parallel to the blades of the spatula at one end of the handle or at the opposite end of the latter relative to the spatula. The blades of the spatula merge into a common shank engaged into a common aperture in one end of the handle and are preferably rigidly interconnected intermediate their ends.

4 Claims, 5 Drawing Figures

DENTURE PROSTHETICS TOOL

This invention relates to a tool of the type adapted to be used in the dental art and, in particular, for denture prosthetics.

An imprint for making a denture is now taken in one's mouth by means of a gum-shape piece of wax after having heat-softened the operative face thereof. This heat-softening is now performed by repeatedly pressing a heated metal blade edgewise therein in a progressive lateral shifting sequence along the gum-shape piece. This operation is time-consuming and to such extent that the originally softened portion has resolidified by the time the sequence terminates. Obviously, this is unsatisfactory since the imprint then can hardly be taken and may be misleading.

It is a general object of the present invention to provide a tool of the above type which is better adapted to produce satisfactory heat-softening of the gum-shape piece of wax which is currently used for denture imprint.

It is a more specific object of the present invention to provide a tool of the above type which includes a multi-bladed spatula to produce faster heat-softening of the piece of wax and, consequently, to avoid premature resolidifying of the originally softened portion and wherein the blades of the spatula have their shank portions merging into laterally contacting engagement in the handle for good strength and easy mounting purposes.

The above and other objects and advantages of the present invention will be better understood in the light of the following detailed description of preferred embodiments thereof which are illustrated, by way of example, in the accompanying drawings, wherein.

Figure 1:
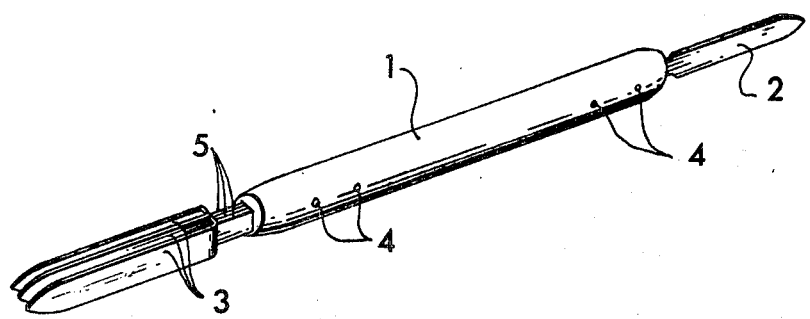
FIG. 1 is a perspective view of a denture prosthetics tool according to a first embodiment of the present invention.

The denture prosthetics tool according to the present invention generally includes an elongated handle 1, of any suitable material, a cutting blade 2 and a multi-bladed spatula comprising blades 3. Each blade 2 or 3 includes a shank portion engaged into an axial aperture in the corresponding end of the elongated handle 1. These shank portions are secured in any suitable manner, such as by transverse pins or rivets 4. All the blades 3 of the spatula are positioned in parallel spaced-apart relationship and have their shank portion 5 merged into lateral engagement to form a common shank engaged in a common axial aperture in the corresponding end of the handle 1.

Figure 2:
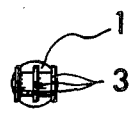
FIG. 2 is an end view of the tool of FIG. 1 as seen from the left in the latter.
Figure 3:
FIG. 3 is a plan view of the tool of FIG. 1.
Figure 4:
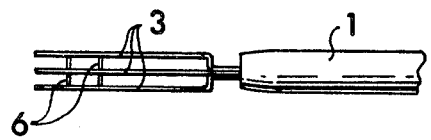
FIG. 4 is a partial plan view of a denture prosthetics tool according to a second embodiment of the invention.

In the embodiment of FIG. 4, as in the embodiment of FIGS. 1, 2, and 3, the spatula is secured at one end of the handle while the service blade 2 is secured at the other and projects in axially opposite direction relative to the blades 3. In the second and third embodiments, shown in FIGS. 4 and 5, respectively, the blades 3 of the spatula are rigidly interconnected intermediate their ends by pins 6 extending transversely therethrough.

Figure 5:
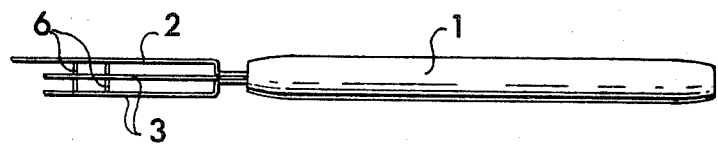
FIG. 5 is a plan view of a denture prosthetics tool according to a third embodiment of the invention.

In the embodiment of FIG. 5, the service blade 2 is secured at the same end of the handle 1 as the blades 3 but is longer than the latter to allow scraping action therewith.

The service blade 2 serves to scrape the usual gum-shape piece of wax while the blades 3 of the spatula are heated and sunk edgewise into the operative face of the wax to soften the latter. The service blade 2 is also provided to perform the other service of holding or straightening a tooth in the wax.

It must be noted that all the blades 2 and 3 extend straight endwise from one end of the elongated handle and in parallel spaced-apart relationship and thus allow reversible use of the blades and tool on either of two opposite sides of the handle. As shown in the drawing, the blades symmetrically project edgewise on the abovementioned sides relative to the elongated handle.

Since none of the blades 2 and 3 has the function of cutting, the laterally opposite edges thereof are preferably blunt to produce better heating contact with the piece of wax.

We claim:

1. A tool for denture prosthetics comprising an elongated handle, a service blade and a multi-bladed spatula including a plurality of blades, with all said blades secured in one end of the elongated handle and projecting straight endwise from the latter in parallel spaced-apart relationship, thereby allowing reversible use of said blades on either of two opposite sides of the handle, and said service blade having a free end projecting farther than the blades of the spatula relative to said handle.

2. A tool as defined in claim 1, wherein all said blades symmetrically project edgewise on said opposite sides relative to the elongated handle.

3. A denture prosthetics tool as defined in claim 2, wherein the blades include each a shank portion inserted into said handle and laterally surrounded by the latter in laterally contacting engagement one with another.

4. A denture prosthetics tool as defined in claim 3, wherein said spatula includes at least one pin projecting transversely through said blades and rigidly interconnecting the latter intermediate their ends.

* * * * *